US00PP32465P2

(12) United States Plant Patent
Kremer-Köhne et al.

(10) Patent No.: US PP32,465 P2
(45) Date of Patent: Nov. 17, 2020

(54) AVOCADO ROOTSTOCK NAMED 'MERENSKY 6'

(50) Latin Name: ***Persea americana* Mill**
Varietal Denomination: Merensky 6

(71) Applicants: Westfalia Fruit Estate Pty Ltd, Tzaneen (ZA); South African Avocado Growers Association, Tzaneen (ZA)

(72) Inventors: Sylvie Kremer-Köhne, Haenertsburg (ZA); Zelda van Rooyen, Tzaneen (ZA)

(73) Assignees: Westfalia, Fruit Estate Pty Ltd, Tzaneen (ZA); South African Avocado Growers Association, Tzaneen (ZA)

( * ) Notice: Subject to any disclaimer, the term of this patent is extended or adjusted under 35 U.S.C. 154(b) by 0 days.

(21) Appl. No.: 16/602,696

(22) Filed: Nov. 20, 2019

(51) Int. Cl.
*A01H 5/08* (2018.01)
*A01H 6/52* (2018.01)

(52) U.S. Cl.
USPC ..... Plt./200

(58) Field of Classification Search
USPC ..... Plt./200
See application file for complete search history.

(56) References Cited

U.S. PATENT DOCUMENTS

| | | | |
|---|---|---|---|
| PP139 | P | 8/1935 | Hass |
| PP15,309 | P3 | 11/2004 | Köhne |
| PP17,947 | P3 | 8/2007 | Darvas |

*Primary Examiner* — Susan McCormick Ewoldt
(74) *Attorney, Agent, or Firm* — Kelly & Kelley, LLP

(57) ABSTRACT

A new and distinct variety of *Persea americana* tree imparting high bearing capacity and vigor to the scion cultivar when used as a rootstock. Further, this rootstock exhibits a high tolerance to *Phytophthora cinnamomi*.

6 Drawing Sheets

Latin name of the genus and species: *Persea americana* Mill.

Varietal denomination: 'Merensky 6'.

BACKGROUND OF THE INVENTION

The present invention is generally directed to a new avocado plant, or variety of *Persea americana* Mill. The varietal denomination of the avocado rootstock of the present application is 'Merensky 6'.

*Phytophthora* is a genus of plant-damaging oomycetes (water molds), capable of causing enormous economic losses on crops worldwide. *Phytophthora cinnamomi* is a soil-borne water mold that produces an infection which causes a condition in plants called "root rot" or "dieback". The plant pathogen is one of the world's most invasive species and is present in over seventy countries around the world. It is distributed worldwide and causes damage on hundreds of hosts. The disease affects a range of economic groups, such as food crops including avocados. It is a root pathogen that causes root rot and death of host plants. *Phytophthora cinnamomi* is the leading cause of damage to avocado trees amongst avocado farmers. Damaged trees generally die or become unproductive within three to five years. The discovery and utilization of avocado varieties, including rootstocks, which are resistant or have a tolerance to *Phytophthora cinnamomi* is highly desirable.

Currently, the main avocado variety grown and consumed in the world is 'Hass' (U.S. Plant Pat. No. 139, the contents of which are incorporated herein by reference). The main markets have year-round supply of 'Hass' avocados and end consumers are very used to buying 'Hass'. Many other avocado varieties have been created and patented over the years, but none of them have been able to obtain important interest from growers, primarily due to the market still preferring the 'Hass' avocado fruit. It would be very desirable to be able to graft 'Hass' trees onto a rootstock which bear good yields.

SUMMARY OF THE INVENTION

This invention relates to a new and distinct avocado variety. The invention 'Merensky 6' is an avocado rootstock characterized by superior tolerance to *Phytophthora* root rot, as compared to 'Duke 7' (not patented). In addition, 'Hass' grafted onto 'Merensky 6' bears more fruits than 'Hass' grown on 'Duke 7' and '3-29-5' grown on 'Merensky 2' (U.S. Plant Pat. No. 15,309).

To generate high yielding new avocado rootstocks tolerant to *Phytophthora cinnamomi* a breeding program was initiated at Tzaneen, Limpopo Province, South Africa in the early 1990s. The avocado rootstock breeding block contained 20 different rootstocks which have shown superior performance under *Phytophthora cinnamomi* pressure (e.g. 'D9' (not patented), 'Duke 7', 'Merensky 1' (U.S. Plant Pat. No. 17,497) and 'Merensky 2'). These trees were used as parent trees for breeding and underwent open pollination. Seeds from the breeding block were germinated and seedlings were screened for their tolerance to root rot by exposure to a virulent strain of *Phytophthora cinnamomi* in a mistbed. The seedlings were planted in *Phytophthora cinnamomi* infested vermiculite and evaluated for their root health after six weeks. Selected seedlings were then cloned and re-tested (10 of each) in the mistbed in comparison to 'Duke 7' (2000-2002) and 'Merensky 2' (2003-2005) clonal commercial rootstocks as described above. Rootstocks with better root health than 'Duke 7' and 'Merensky 2' respectively were selected in the second mistbed screening, asexually propagated and grafted with 'Hass' for field evaluation.

'Merensky 6' was developed at Tzaneen, Limpopo Province, South Africa. The 'Merensky 6' rootstock variety originated from the avocado breeding block in 1993. The maternal parent is the 'D9' avocado variety. The pollen parent is unknown. Fruits were collected from the breeding block, the seeds removed and planted in vermiculite. The seedlings were grown under a shade net. When the seedlings were approximately 30 cm tall they were transplanted in *Phytophthora cinnamomi* infested vermiculite and evaluated for their root health after six weeks.

Based on its tolerance to the disease, 'Merensky 6' was selected as a single plant for further evaluation. Budwood was collected from the plant and grafted to stumps of adult avocado trees that had been cut down in the avocado genepool orchard. 'Merensky 6' grew into trees which provided budwood for producing clonal trees, using the nurse seed/etiolation system, for further testing.

During screening and field evaluation, 'Merensky 6' differed from other varieties by having a high tolerance against *Phytophthora* root rot as well as high bearing capacity. The traits of 'Merensky 6' were found to be stable and progeny formed by asexual propagation is true to type.

BRIEF DESCRIPTION OF THE DRAWINGS

The accompanying photographs show specimens of the tree and plant parts of the new 'Merensky 6' variety.

DETAILED BOTANICAL DESCRIPTION OF THE VARIETY

The following is a detailed description of the new 'Merensky 6' variety, which was taken from approximately 4-year-old mature trees, with the exception as a rootstock for a specific scion when reference is made to root rot tolerance and yield. The trees are located in an experimental orchard at Tzaneen, Limpopo Province, South Africa, and are grafted on a 'Merensky 2' rootstock.

In those instances where precise color assessment could be made, The Royal Horticulture Society (R.H.S.) color numbering system (R.H.S. Colour Chart published by The Royal Horticultural Society, London 2001) is used herein for the color description of the rind, seed, bark, leaf, flower, flesh color and other characters of the 'Merensky 6' avocado tree. In other instances, generally, color terms are used in accordance with an ordinary dictionary significance.

Figure 1:
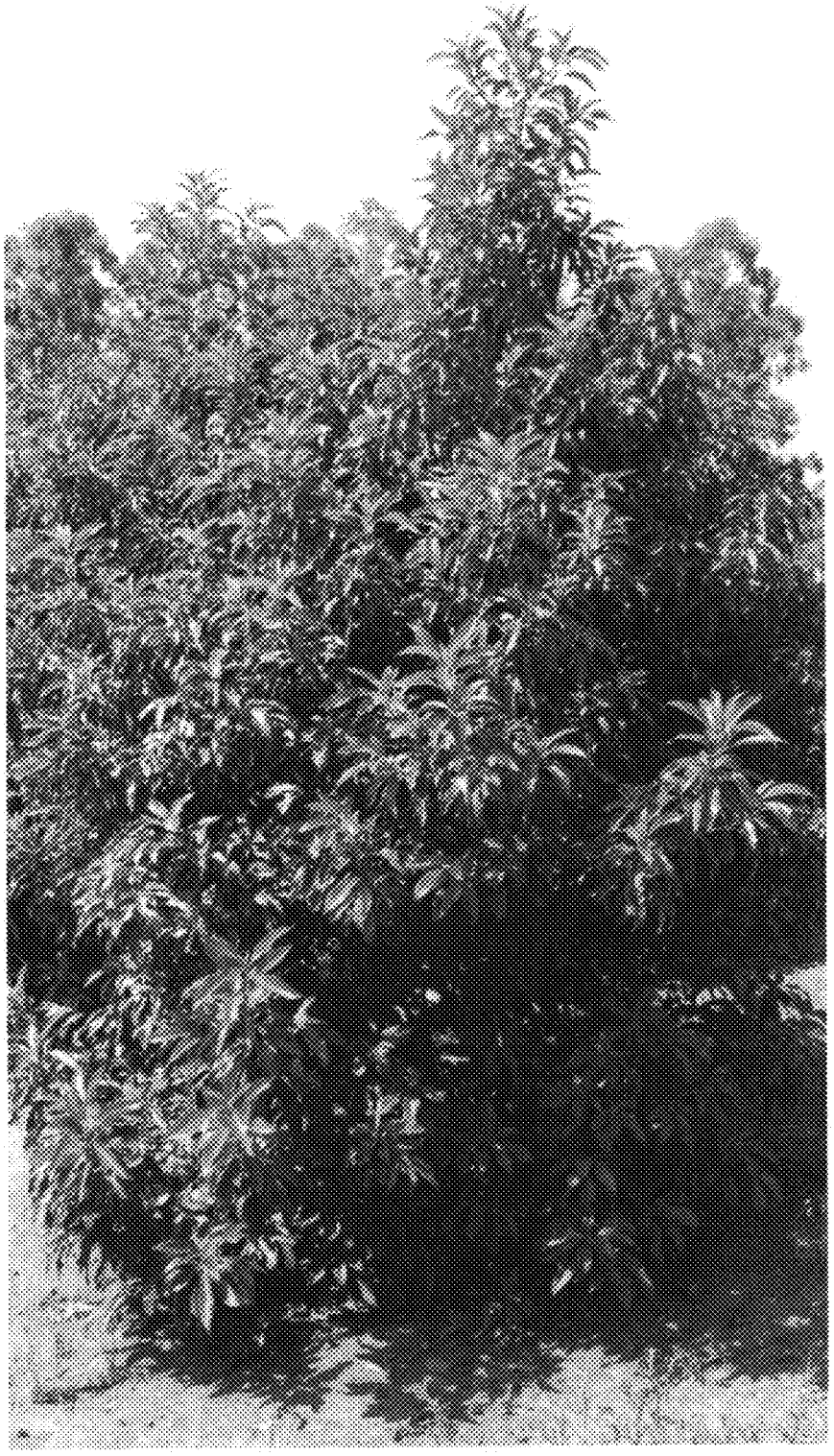
FIG. 1 is a photograph depicting a four-year-old, top-worked tree of the 'Merensky 6' variety while growing in Tzaneen, Limpopo Province, South Africa

With reference now to FIG. 1, the 'Merensky 6' tree has an upright and vigorous growth habit. Below in Table 1 are data on the vigor of 'Hass' grafted onto the rootstock of 'Merensky 6' as determined by trunk diameter measurements, taken 20 cm from the soil line, from trees planted in an orchard with *Phytophthora cinnamomi* in Tzaneen, Limpopo Province, South Africa.

TABLE 1

| | Trunk diameter (cm) | | | | |
|---|---|---|---|---|---|
| Rootstock | Year 2 | Year 3 | Year 4 | Year 5 | Year 6 |
| 'Merensky 6' | 7.1 ± 1.1 | 8.6 ± 1.4 | 11.4 ± 1.7 | 13.7 ± 2.0 | 16.2 ± 2.2 |
| 'Duke 7' | 5.6 ± 1.0 | 6.5 ± 1.1 | 8.2 ± 1.3 | 9.3 ± 1.5 | 10.8 ± 1.7 |

Tzaneen, Limpopo Province, South Africa, with 'Hass' scion (n = 24)

Below are data on the vigor of 'Hass' grafted onto the rootstock of 'Merensky 6' as determined by trunk diameter measurements, taken 5 cm from the soil line, from trees planted in an orchard with *Phytophthora cinnamomi* in Goleta, Calif., USA.

TABLE 2

| | Trunk diameter (cm) | | |
|---|---|---|---|
| Rootstock | Year 2 | Year 3 | Year 4 |
| 'Merensky 6' | 6.1 ± 3.8 | 9.4 ± 0.7 | 11.2 ± 1.0 |
| 'Merensky 2' | 6.8 ± 3.1 | 8.4 ± 2.7 | 11.4 ± 1.2 |

Goleta, California, USA, with 'Hass' scion (n = 15)

Table 3 below provides the data on the typical canopy size of 'Hass' grafted onto the rootstock of 'Merensky 6' as determined by canopy volume measurements from trees planted in an orchard with negligible *Phytophthora cinnamomi* and salinity levels in Goleta, Calif., USA.

TABLE 3

| | Canopy volume ($m^3$) | | |
|---|---|---|---|
| Rootstock | Year 2 | Year 3 | Year 4 |
| 'Merensky 6' | 9.2 ± 2.2 | 11.1 ± 2.3 | 15.2 ± 1.1 |
| 'Merensky 2' | 7.7 ± 3.0 | 10.5 ± 2.9 | 17.0 ± 1.9 |

Goleta, California, USA, with 'Hass' scion (n = 15)

Figure 2:
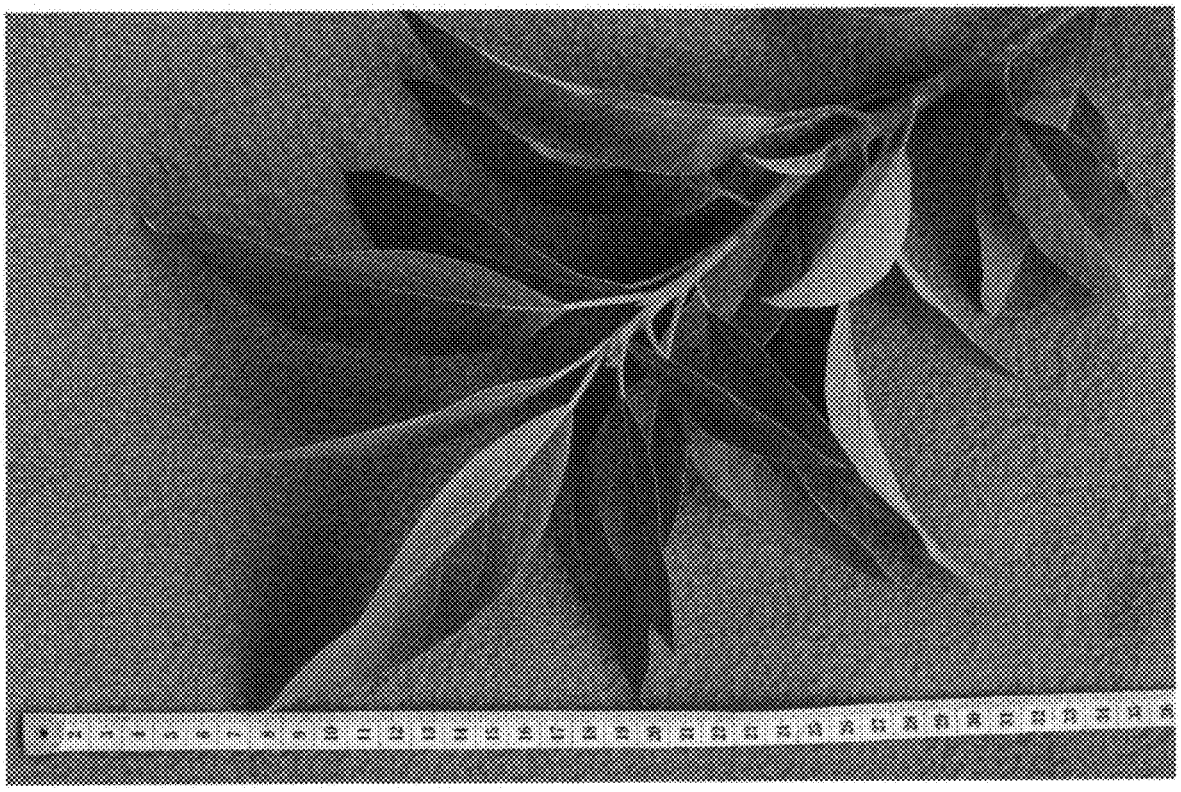
FIG. 2 is a photograph depicting typical mature foliage of the 'Merensky 6' variety, above a tape measure in centimeters for size reference.
Figure 3:
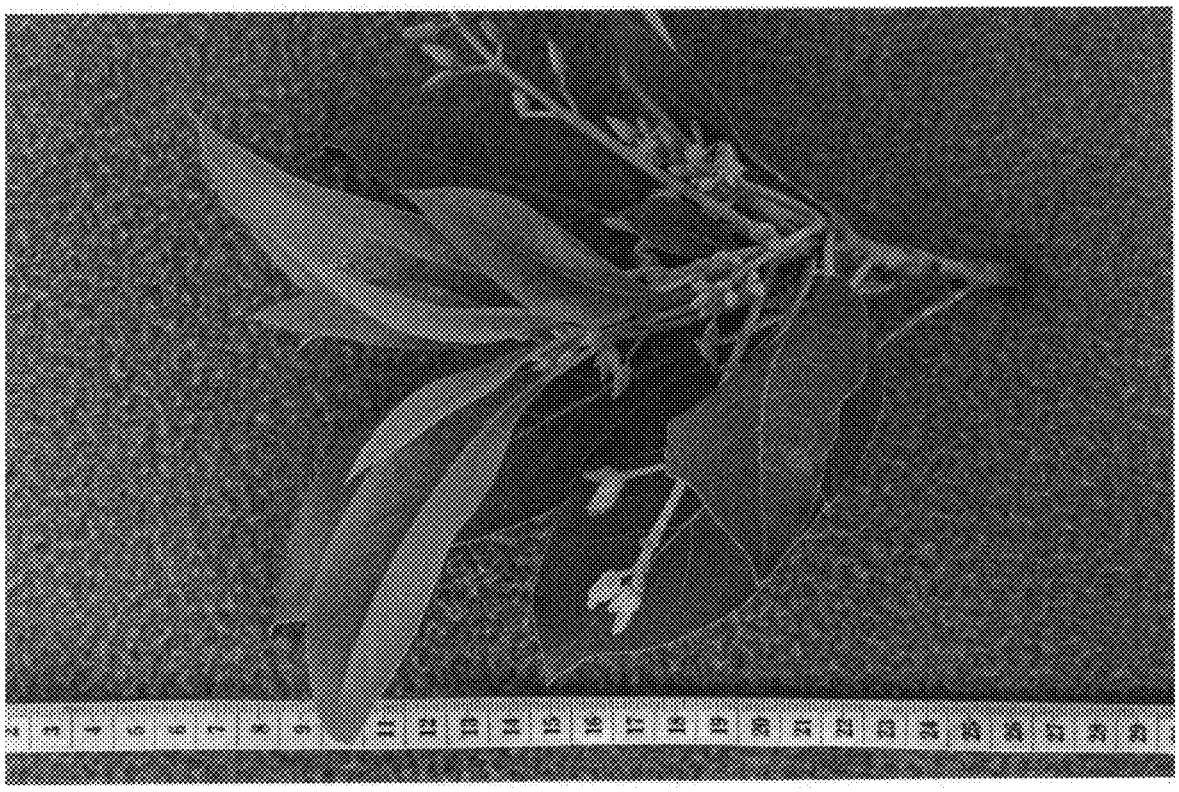
FIG. 3 is a photograph depicting typical flush foliage of the 'Merensky 6' variety, above a tape measure in centimeters for size reference.
Figure 4:
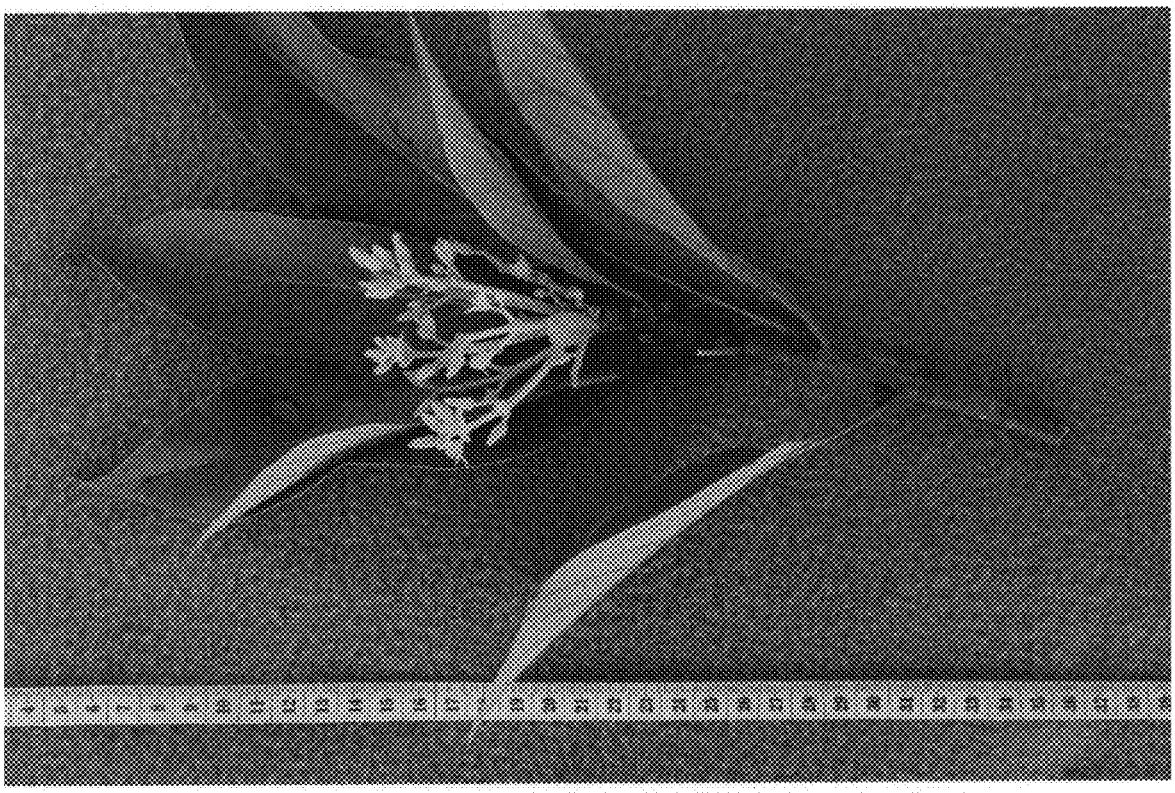
FIG. 4 is a photograph depicting typical inflorescence of the 'Merensky 6' variety, above a tape measure in centimeters for size reference.
Figure 5:
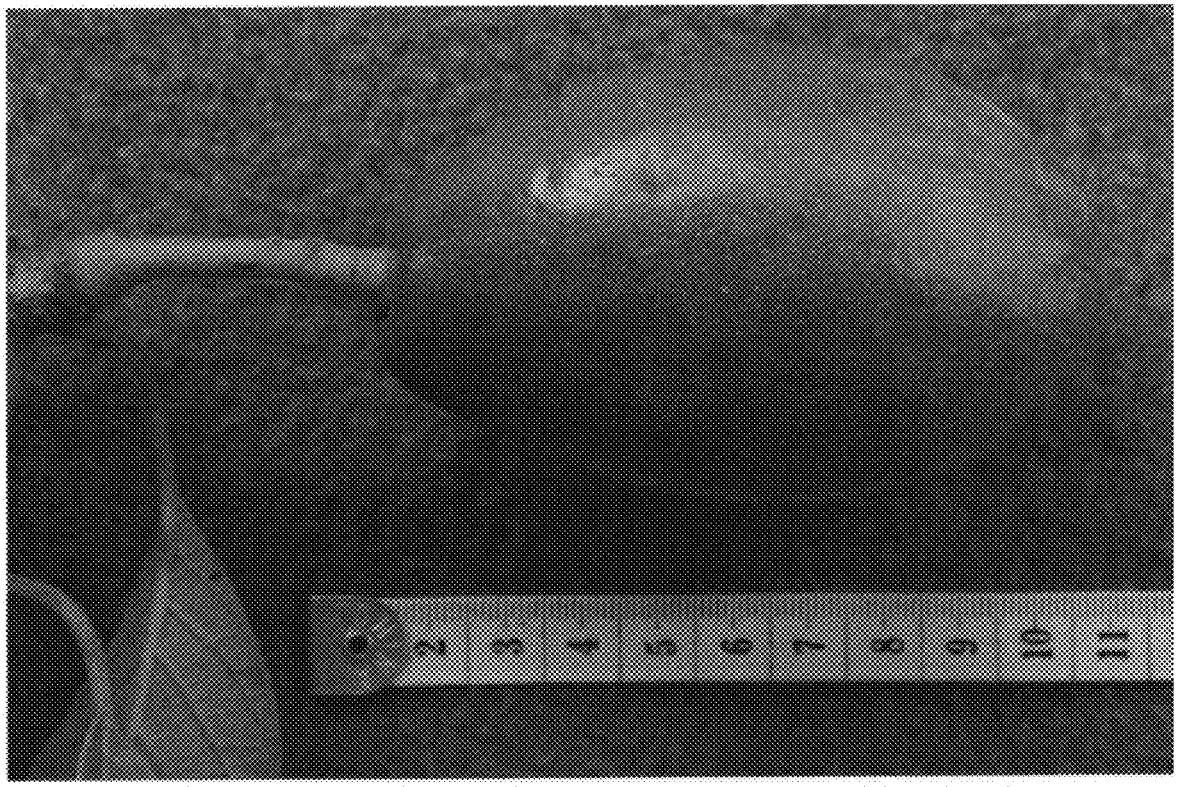
FIG. 5 is a photograph depicting a typical external view of the fruit of the 'Merensky 6' variety, above a tape measure in centimeters for size reference.
Figure 6:
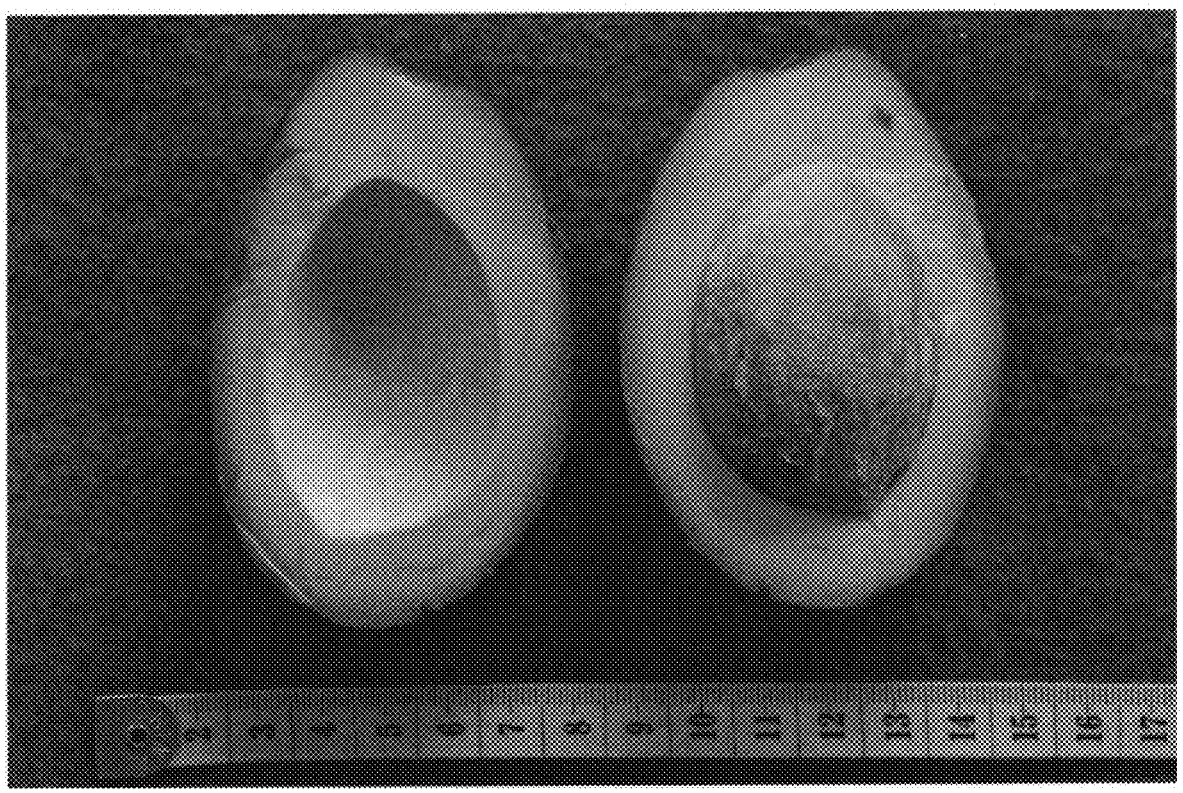
FIG. 6 is a photograph depicting typical internal views of the fruit of the 'Merensky 6' variety, with and without the seed, above a tape measure in centimeters for size reference.

With reference now to FIGS. 2-4, the color of a one-year-old branch of 'Merensky 6' is yellow-green (RHS 146B). The bark of the one-year-old old branch is smooth. The lenticels of the one-year-old branch are inconspicuous.

The color of the main stem is grey-brown (RHS 199A). The texture of the bark of the main stem is corky.

The young shoot (flush) has a very weak intensity of anthocyanin coloration. The color of the young shoot is yellow-green (RHS 146A). The conspicuousness of lenticels is high. The lenticels of the young shoot are greyed-purple (RHS 185B). By comparison, lenticels of 'Duke 7' are green (RHS 139B). The size of the lenticels of the young shoot of the 'Merensky 6' is approximately 1.0 mm long. There are approximately +/−20 lenticels per square cm. The color of the upper side of the young shoot is yellow-green (RHS 146A). The upper side of the young shoot has high glossiness. The lower surface of the young shoot has a yellow-green (RHS 146B) color.

A mature leaf of the 'Merensky 6' variety has a length of approximately 19.0 cm and a width of approximately 6.0 cm, for a length/width ratio of 3.2. The shape of the mature leaf is lanceolate. The color of the upper side of the mature leaf is green (RHS 137A), and has a medium glossiness. The lower side of a mature leaf of the 'Merensky 6' leaf is green (RHS N138C). Veins are prominent and in relief on the lower side of the mature leaf. The color of the veins is yellow-green (RHS 151A). The mature leaves have a generally flat shape and cross-section. The color of the petiole of a mature leaf is yellow-green (RHS 144C). The length of the leaf petiole is approximately 3.7 cm. The mature leaf has a medium anise aroma. The margin of the mature leaf has a weak undulation. Reflexing of apex is present. The mature leaf apex shape and base shape are both acute. The leaves are held horizontally, i.e., approximately perpendicular to the shoot.

The bud shape of the 'Merensky 6' flower is ovoid. The bud size is approximately 5 mm in length and approximately 4 mm in diameter. The bud color is yellow-green (RHS 145A). The flower belongs to Group "A", with female opening occurring in the morning and ending before noon. The male opening occurs in the afternoon of the next day. The flower's opening cycle lasts approximately 30-36 hours. The petals of the flower are borne in two whorls of three perianth lobes. The petals possess entire margins and petal coloration is yellow-green (RHS 145C). There are commonly nine fertile stamens, each having two basal orange nectar glands and three staminodia. The anthers are tetrathecal. The single pistil with a slender style and small stigmatic surface has one carpel with one ovule. The ovary is superior. The pedicel is commonly approximately 2.3 mm in length and approximately 1.2 mm in diameter. The coloration of the pedicel is yellow-green (RHS 145A). There are approximately 60-80 flowers per inflorescence. Generally, 'Merensky 6' has been found to bloom in July at Tzaneen, Limpopo Province, South Africa. The flowering time in California, USA, has been found to be between March and April.

The fruit of the 'Merensky 6' has a length of approximately 8.7 cm and a width of approximately 5.6 cm, for a ratio length/width of 1.6. The shape of the fruit is ellipsoid. The color of the skin of the fruit, when ripe, is yellow-green (RHS 146A). The texture of the skin of the fruit is smooth. Longitudinal ridges are absent. The thickness of the skin of the fruit is moderately thin. There is an intermediate adherence of the skin to the flesh of the fruit. The main color of the flesh is yellow-green (RHS 154C). The color of the intensely colored area of flesh next to the skin is yellow-green (RHS 144A). The width of the intensely colored area of flesh next to the skin is approximately 3.0 mm. Fibers in the flesh are conspicuous.

The seed of the 'Merensky 6' has a length of approximately 5.1 cm and a width of approximately 3.6 cm, on average. The shape, in longitudinal section, is ovate, and circular in cross-section. The color of the seed coat (fresh) is greyed-orange (RHS 166B).

The 'Merensky 6' fruit ripen in February in Tzaneen, Limpopo Province, South Africa; and in September in California, USA. The fruit of 'Merensky 6' are not intended for market use. Instead, the variety is intended to be used as a vegetatively propagated rootstock onto which commercial varieties such as 'Hass', are grafted.

Table 4 through Table 8 provide data on the yield of the 'Merensky 6' rootstock as compared to other rootstocks, for various scions and locations in South Africa and California. The data from these tables, taken from field trials, show that the 'Merensky 6' rootstock imparts a high bearing capacity to the scion.

TABLE 4

| | Yield (kg/tree) | | |
|---|---|---|---|
| Rootstock | Year 2 | Year 3 | Year 4 |
| 'Merensky 6' | 0.3 ± 0.5 | 4.6 ± 5.3 | 0 |
| 'Duke 7' | 0.3 ± 0.6 | 1.2 ± 1.1 | 0 |
| | Yield (kg/tree) | | |
| Rootstock | Year 5 | Year 6 | Cumulative |
| 'Merensky 6' | 40.7 ± 12.4 | 38.0 ± 19.3 | 83.6 ± 28.6 |
| 'Duke 7' | 16.9 ± 10.3 | 6.3 ± 11.8 | 24.7 ± 17.5 |

Tzaneen, Limpopo Province, South Africa, with 'Hass' scion (n = 24)

TABLE 5

| | Yield (kg/tree) | | | |
|---|---|---|---|---|
| Rootstock | Year 2 | Year 3 | Year 4 | Year 5 |
| 'Merensky 6' | 19.7 ± 10.3 | 46.8 ± 19.6 | 16.3 ± 9.0 | 73.3 ± 24.1 |
| 'Merensky 2' | 13.4 ± 10.5 | 42.2 ± 14.6 | 19.9 ± 12.0 | 59.8 ± 24.1 |
| | Yield (kg/tree) | | | |
| Rootstock | Year 6 | Year 7 | Year 8 | Cumulative |
| 'Merensky 6' | 18.9 ± 21.8 | 34.7 ± 19.4 | 117.9 ± 27.6 | 327.6 ± 83.9 |
| 'Merensky 2' | 21.9 ± 23.5 | 21.8 ± 21.2 | 78.5 ± 18.6 | 257.5 ± 77.1 |

Morebeng, Limpopo Province, South Africa, with '3-29-5' scion (n = 45)

TABLE 6

| | Yield (kg/tree) | | | |
|---|---|---|---|---|
| Rootstock | Year 2 | Year 3 | Year 4 | Year 5 |
| 'Merensky 6' | 31.3 ± 7.4 | 17.5 ± 18.6 | 48.7 ± 22.5 | 74.1 ± 26.9 |
| 'Merensky 2' | 23.5 ± 9.0 | 19.0 ± 15.9 | 34.9 ± 18.3 | 50.6 ± 26.1 |
| | Yield (kg/tree) | | | |
| Rootstock | Year 6 | Year 7 | Year 8 | Cumulative |
| 'Merensky 6' | 72.8 ± 47.3 | 26.2 ± 35.0 | 157.0 ± 47.2 | 427.6 ± 87.3 |
| 'Merensky 2' | 26.3 ± 25.4 | 23.3 ± 20.0 | 107.0 ± 41.1 | 284.6 ± 88.5 |

Morebeng, Limpopo Province, South Africa, with 'Hass' scion (n = 45)

TABLE 7

| | Yield (kg/tree) | | |
|---|---|---|---|
| Rootstock | Year 2 | Year 3 | Year 4 |
| 'Merensky 6' | 22.4 ± 10.6 | 12.6 ± 14.0 | 19.5 ± 11.7 |
| 'Merensky 2' | 14.9 ± 11.5 | 12.2 ± 11.4 | 16.4 ± 13.9 |

TABLE 7-continued

| Rootstock | Yield (kg/tree) | | |
|---|---|---|---|
| | Year 5 | Year 6 | Cumulative |
| 'Merensky 6' | 11.9 ± 11.3 | 15.6 ± 15.7 | 81.9 ± 21.4 |
| 'Merensky 2' | 7.4 ± 9.5 | 8.9 ± 10.1 | 59.8 ± 31.0 |

Santa Paula, California, USA, with 'Hass' scion (n = 10)

TABLE 8

| Rootstock | Yield (kg/tree) | | | |
|---|---|---|---|---|
| | Year 2 | Year 3 | Year 4 | Cumulative |
| 'Merensky 6' | 8.3 ± 5.5 | 23.0 ± 14.1 | 14.0 ± 14.1 | 45.3 ± 17.1 |
| 'Merensky 2' | 4.2 ± 5.3 | 23.7 ± 10.0 | 14.0 ± 9.5 | 41.8 ± 16.5 |

Goleta, California, USA, with 'Hass' scion (n = 15)

As shown in Table 9 and Table 10 below, which represent data of tree health of the 'Hass' scion on 'Merensky 6' as compared to using 'Merensky 2', 'Hass' trees on the 'Merensky 6' rootstock are healthier than those on the 'Merensky 2' rootstock.

TABLE 9

| Rootstock | Tree Health (0-10; 10 = Dead) |
|---|---|
| 'Merensky 6' | 0.1 ± 0.3 |
| 'Merensky 2' | 3.2 ± 0.8 |

Santa Paula, California, USA, with 'Hass' scion, 6-year-old trees (n = 10)

TABLE 10

| Rootstock | Tree Health (0-10; 10 = Dead) |
|---|---|
| 'Merensky 6' | 1.1 ± 1.8 |
| 'Merensky 2' | 1.9 ± 3.6 |

Goleta, California, USA, with 'Hass' scion, 4-year-old trees (n = 15)

The 'Merensky 6' variety and rootstock have shown a strong tolerance to *Phytophthora cinnamomi*.

What is claimed is:

1. A new and distinct rootstock variety of avocado tree having the characteristics as described and illustrated herein.

* * * * *